(12) United States Patent
Seebeck et al.

(10) Patent No.: US 8,308,807 B2
(45) Date of Patent: Nov. 13, 2012

(54) IMPLANT WITH DIFFERENTIAL ANCHORING

(75) Inventors: Jörn Seebeck, Kollbrunn (CH); Eik Siggelkow, Kollbrunn (CH)

(73) Assignee: Zimmer, GmbH, Winterthur (CH)

( * ) Notice: Subject to any disclaimer, the term of this patent is extended or adjusted under 35 U.S.C. 154(b) by 626 days.

(21) Appl. No.: 12/162,729

(22) PCT Filed: Nov. 9, 2006

(86) PCT No.: PCT/EP2006/068318
§ 371 (c)(1),
(2), (4) Date: Nov. 24, 2008

(87) PCT Pub. No.: WO2007/054553
PCT Pub. Date: May 18, 2007

(65) Prior Publication Data
US 2009/0105772 A1    Apr. 23, 2009

(30) Foreign Application Priority Data

Nov. 9, 2005 (CH) .................................. 1820/05

(51) Int. Cl.
*A61F 2/38* (2006.01)
(52) U.S. Cl. .................. 623/20.14; 606/329; 606/297
(58) Field of Classification Search .............. 606/297, 606/286, 280, 329; 623/19.11–19.14, 20.14, 623/20.21, 20.32
See application file for complete search history.

(56) References Cited

U.S. PATENT DOCUMENTS 1,448,111 A    3/1923    Eppler
(Continued)

FOREIGN PATENT DOCUMENTS

DE    1164019    2/1964
(Continued)

OTHER PUBLICATIONS

Quinton, J.S. and P.C. Dastoor, "Characterizing the bonding mechanisms at silane-metal interfaces: a model system", J. Mat. Sci. Letters, vol. 18, Nov. 1999, pp. 1833-1835.

*Primary Examiner* — Thomas Barrett
*Assistant Examiner* — Melissa A Golob
(74) *Attorney, Agent, or Firm* — Schwegman, Lundberg & Woessner, P.A.

(57) ABSTRACT

An implant (10) for anchoring on a bone (1) has a plurality of anchoring pins (20) which extend away from a fastening side of the implant and are provided for anchoring the implant in the bone. In different areas of the fastening side of the implant, the pin arrangement and/or the geometry of the pins are chosen differently. In particular, in different areas of the fastening side of the implant, the volume of the anchoring pins (20) per unit of surface area of the fastening side of the implant is different, preferably in such a way that the geometry and/or arrangement of the pins (20) is chosen according to the proportion of bone tissue in the total tissue of the bone substance, opposite which the area of the fastening side is provided, in such a way that, in areas where there is a relatively higher proportion of bone tissue as a whole, less tissue is displaced by the anchoring pins than in areas where there is a relatively smaller proportion of bone tissue.

24 Claims, 12 Drawing Sheets

U.S. PATENT DOCUMENTS

Figure 1A:
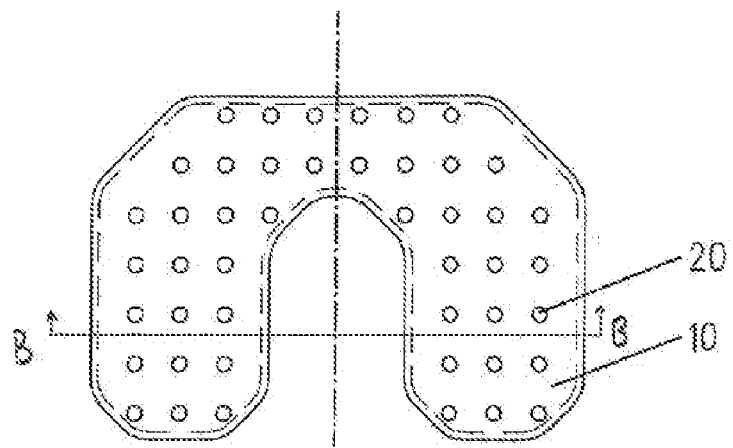

| | | | |
|---|---|---|---|
| 4,312,079 A | 1/1982 | Dorre et al. | |
| 4,355,429 A * | 10/1982 | Mittelmeier et al. | 623/20.14 |
| 4,467,479 A | 8/1984 | Brody | |
| 4,502,161 A | 3/1985 | Wall | |
| 4,659,331 A * | 4/1987 | Matthews et al. | 623/20.21 |
| 4,769,039 A | 9/1988 | Horber | |
| 4,839,215 A | 6/1989 | Starling et al. | |
| 4,865,603 A * | 9/1989 | Noiles | 623/23.5 |
| 4,896,663 A | 1/1990 | Vandewalls | |
| 4,932,969 A | 6/1990 | Frey et al. | |
| 4,966,924 A | 10/1990 | Hyon et al. | |
| 4,976,740 A | 12/1990 | Kleiner | |
| 5,032,132 A * | 7/1991 | Matsen et al. | 623/19.11 |
| 5,041,138 A | 8/1991 | Vacanti et al. | |
| 5,080,678 A | 1/1992 | Spotorno et al. | |
| 5,147,904 A | 9/1992 | Jochum et al. | |
| 5,217,498 A | 6/1993 | Henssge et al. | |
| 5,246,459 A | 9/1993 | Elias | |
| 5,271,737 A | 12/1993 | Baldwin et al. | |
| 5,282,861 A | 2/1994 | Kaplan | |
| 5,312,409 A | 5/1994 | McLaughlin et al. | |
| 5,314,478 A | 5/1994 | Oka et al. | |
| 5,358,525 A | 10/1994 | Fox et al. | |
| 5,370,700 A | 12/1994 | Sarkisian et al. | |
| 5,458,643 A | 10/1995 | Oka et al. | |
| 5,553,476 A | 9/1996 | Oehy et al. | |
| 5,556,429 A | 9/1996 | Felt | |
| 5,607,474 A | 3/1997 | Athanasiou et al. | |
| 5,609,641 A | 3/1997 | Johnson et al. | |
| 5,645,592 A | 7/1997 | Nicolais et al. | |
| 5,658,343 A | 8/1997 | Hauselmann et al. | |
| 5,795,353 A | 8/1998 | Felt | |
| 5,800,551 A * | 9/1998 | Williamson et al. | 623/19.11 |
| 5,817,098 A | 10/1998 | Albrektsson et al. | |
| 5,871,541 A | 2/1999 | Gerber | |
| 5,951,564 A | 9/1999 | Schroder et al. | |
| 6,132,468 A | 10/2000 | Mansmann | |
| 6,140,452 A | 10/2000 | Felt et al. | |
| 6,168,630 B1 | 1/2001 | Keller et al. | |
| 6,224,630 B1 | 5/2001 | Bao et al. | |
| 6,231,605 B1 | 5/2001 | Ku | |
| RE37,277 E | 7/2001 | Baldwin et al. | |
| 6,306,177 B1 | 10/2001 | Felt et al. | |
| 6,425,923 B1 | 7/2002 | Stalcup et al. | |
| 6,428,577 B1 * | 8/2002 | Evans et al. | 623/20.29 |
| 6,443,988 B2 | 9/2002 | Felt et al. | |
| 6,447,514 B1 | 9/2002 | Stalcup et al. | |
| 6,494,917 B1 | 12/2002 | McKellop et al. | |
| 6,530,956 B1 | 3/2003 | Mansmann | |
| 6,533,818 B1 | 3/2003 | Weber et al. | |
| 6,547,828 B2 | 4/2003 | Scott et al. | |
| 6,620,196 B1 | 9/2003 | Trieu | |
| 6,629,997 B2 | 10/2003 | Mansmann | |
| 6,652,587 B2 | 11/2003 | Felt et al. | |
| 6,652,588 B2 | 11/2003 | Hayes, Jr. et al. | |
| 6,679,913 B2 | 1/2004 | Homsy | |
| 6,719,797 B1 | 4/2004 | Ferree | |
| 6,827,743 B2 | 12/2004 | Eisermann | |
| 6,994,730 B2 | 2/2006 | Posner | |
| 7,001,431 B2 | 2/2006 | Bao et al. | |
| 7,077,865 B2 | 7/2006 | Bao et al. | |
| 2001/0033857 A1 | 10/2001 | Vyakaman et al. | |
| 2001/0039455 A1 | 11/2001 | Simon et al. | |
| 2002/0022884 A1 | 2/2002 | Mansmann | |
| 2002/0029083 A1 | 3/2002 | Zucherman et al. | |
| 2002/0127264 A1 | 9/2002 | Felt et al. | |
| 2002/0156531 A1 | 10/2002 | Felt et al. | |
| 2002/0161448 A1 | 10/2002 | Hayes, Jr. et al. | |
| 2002/0173852 A1 | 11/2002 | Felt et al. | |
| 2002/0173855 A1 | 11/2002 | Mansmann | |
| 2002/0183845 A1 | 12/2002 | Mansmann | |
| 2002/0183850 A1 | 12/2002 | Felt et al. | |
| 2002/0188300 A1 | 12/2002 | Arramon et al. | |
| 2002/0193883 A1 | 12/2002 | Wironen | |
| 2003/0008396 A1 | 1/2003 | Ku | |
| 2003/0074076 A1 | 4/2003 | Ferree et al. | |
| 2003/0078617 A1 | 4/2003 | Schwartz et al. | |
| 2003/0130741 A1 | 7/2003 | McMinn | |
| 2003/0153918 A1 | 8/2003 | Putnam et al. | |
| 2003/0163202 A1 | 8/2003 | Lakin | |
| 2003/0195628 A1 | 10/2003 | Bae et al. | |
| 2003/0220649 A1 | 11/2003 | Bao et al. | |
| 2004/0010312 A1 | 1/2004 | Enayati | |
| 2004/0039447 A1 | 2/2004 | Simon et al. | |
| 2004/0051213 A1 | 3/2004 | Muratoglu | |
| 2004/0107000 A1 | 6/2004 | Felt et al. | |
| 2004/0133275 A1 | 7/2004 | Mansmann | |
| 2004/0138754 A1 | 7/2004 | Lang et al. | |
| 2004/0153163 A1 | 8/2004 | Posner | |
| 2004/0163681 A1 | 8/2004 | Verhaverbeke | |
| 2004/0199250 A1 | 10/2004 | Fell | |
| 2004/0220582 A1 | 11/2004 | Keller | |
| 2004/0236424 A1 | 11/2004 | Berez et al. | |
| 2004/0247641 A1 | 12/2004 | Felt et al. | |
| 2004/0267371 A1 | 12/2004 | Hayes, Jr. et al. | |
| 2005/0021042 A1 | 1/2005 | Marnay et al. | |
| 2005/0043808 A1 | 2/2005 | Felt et al. | |
| 2005/0075642 A1 | 4/2005 | Felt et al. | |
| 2005/0125077 A1 | 6/2005 | Harmon et al. | |
| 2005/0171604 A1 | 8/2005 | Michalow | |
| 2005/0251149 A1 | 11/2005 | Wenz | |
| 2005/0251266 A1 | 11/2005 | Maspero et al. | |
| 2005/0287187 A1 | 12/2005 | Mansmann | |
| 2006/0009853 A1 | 1/2006 | Justin et al. | |
| 2006/0079905 A1 | 4/2006 | Beyar et al. | |
| 2006/0224244 A1 | 10/2006 | Thomas et al. | |
| 2006/0235542 A1 | 10/2006 | Hodorek et al. | |
| 2006/0253200 A1 | 11/2006 | Bao et al. | |
| 2007/0027230 A1 | 2/2007 | Beyar et al. | |
| 2007/0038300 A1 | 2/2007 | Bao et al. | |
| 2007/0088444 A1 | 4/2007 | Hodorek et al. | |
| 2007/0142916 A1 | 6/2007 | Olson et al. | |
| 2007/0179607 A1 | 8/2007 | Hodorek et al. | |
| 2008/0215057 A1 | 9/2008 | Willi | |
| 2008/0221700 A1 | 9/2008 | Howald et al. | |

FOREIGN PATENT DOCUMENTS

| | | |
|---|---|---|
| DE | 2015324 A1 | 11/1971 |
| DE | 2501080 A1 | 7/1976 |
| DE | 2933174 A1 | 4/1980 |
| DE | 2953575 A1 | 7/1982 |
| DE | 3923418 C2 | 1/1991 |
| DE | 4317448 A1 | 11/1994 |
| DE | 29513894 U1 | 11/1995 |
| DE | 19721661 A1 | 11/1998 |
| DE | 19803183 A1 | 8/1999 |
| DE | 10021387 A1 | 11/2001 |
| DE | 20303205 U1 | 4/2003 |
| DE | 10220368 A1 | 12/2003 |
| DE | 10339605 A1 | 4/2005 |
| EP | 0013863 A1 | 8/1980 |
| EP | 0013864 A1 | 8/1980 |
| EP | 0017930 A1 | 10/1980 |
| EP | 0170779 A1 | 2/1986 |
| EP | 0528080 A1 | 2/1993 |
| EP | 0480954 B1 | 4/1993 |
| EP | 0552949 A1 | 7/1993 |
| EP | 0577529 A1 | 1/1994 |
| EP | 0639356 A1 | 2/1995 |
| EP | 0768066 A2 | 4/1997 |
| EP | 0892627 B1 | 1/1999 |
| EP | 0992222 A2 | 4/2000 |
| EP | 0507645 B1 | 7/2001 |
| EP | 1340477 A2 | 9/2003 |
| EP | 1407728 A1 | 4/2004 |
| EP | 1477120 A1 | 11/2004 |
| EP | 1588669 A1 | 10/2005 |
| FR | 2519545 A | 7/1983 |
| FR | 2691355 A1 | 11/1993 |
| FR | 2692140 A1 | 12/1993 |
| FR | 2803190 A1 | 7/2001 |
| FR | 2803191 A1 | 7/2001 |
| GB | 1126961 A | 11/1968 |
| GB | 1349987 A | 4/1974 |
| GB | 2139097 A | 11/1984 |
| WO | WO97/37613 A1 | 10/1997 |
| WO | WO00/15153 A1 | 3/2000 |

| | | | |
|---|---|---|---|
| WO | WO00/23009 A1 | 4/2000 |
| WO | WO01/45595 A2 | 6/2001 |
| WO | WO02/41808 A1 | 5/2002 |
| WO | WO02/054992 A1 | 7/2002 |
| WO | WO2004/032987 A1 | 4/2004 |
| WO | WO2005/051242 A1 | 6/2005 |
| WO | WO2007/090790 A2 | 8/2007 |
| WO | WO2007/125060 A1 | 11/2007 |

* cited by examiner

IMPLANT WITH DIFFERENTIAL ANCHORING

This application is a U.S. National Phase Patent Application based on International Application Serial No. PCT/EP2006/068318 filed Nov. 9, 2006, the disclosure of which is hereby explicitly incorporated by reference herein.

The invention relates to an implant in accordance with the preamble of claim 1.

Components of joint implants are usually fastened to resection surfaces of bones. Due to naturally given kinematics of the joints, the connection points at which the components of the implants are fastened to the bone are frequently stressed parallel to the connection plane and must also partly be able to absorb tension stresses or tiling stresses which attempt to separate the implant component from the bone.

Such stress forms occur, for example, in the tibial component of a knee joint.

It is known from the prior art, for example, to introduce central shafts into the medullary space of long bones or to provide the component with spigots which take up the fixing of the component on the bone with respect to transverse stress. With glenoid components of shoulder joint prostheses, it is known to screw them or to fix them in the bone with individual spigots.

DE 198 03 183 describes a tibial component as well as a femoral component of a total knee joint prosthesis which have conical bores at their sides facing the bone and provided for the implantation in which fastening pins can be arranged for the fastening of the bone in the implant. In accordance with the teaching communicated there, the pins are positioned such as is most suitable for the respectively present bone structure. A further going specification of this teaching is not communicated by DE 198 03 183, nor does it communicate any teaching for the skilled person which can be realized directly as to which positioning of the pins is suitable for which bone structure.

EP 577 529 sets forth an implant which has pin-shaped anchorage elements arranged in scattered form for fastening to the bone.

EP 013 864 communicates the teaching of anchoring an implant in the bone by means of a few anchorage spigots having a wave-like outer profile.

DE 1 164 019 sets forth a cap for the replacement of the joint surface of a femoral head which is to be anchored by means of three pins. The majority of pins serves for the security against rotation of the cap-shaped implant. The document emphasizes the importance for the teaching communicated there of the anchorage of the pins in the cortical bone tissue of the lateral femur and/or of Adam's arch.

The invention starts from the fact of providing an implant of the initially named kind with pin-shaped anchorage elements which can be introduced into the bone material and displace bone tissue there. A plurality of anchorage pins are in particular used which are in particular arranged as a pin field or in a plurality of pin fields. The implant therefore in particular finds stability not by the fixing by means of individual fastening elements, but rather by the cooperation of the totality of pins which are arranged so-to-say as a bed of nails. The force required for the anchorage of the implant is thus substantially distributed over the total resection surface. Particularly with poor and in particular osteoporotic bone tissue, a local strong stress on the bone tissue is also thereby avoided and the individual regions of the bone in which the introduction of force takes place are substantially distributed over the total resection surface and in particular over the spongious region of the resection surface, whereby the bone receives stimulation to bone growth in the total region of the resection surface. A positive effect is in particular achieved on the bone quality in the total region of the anchorage due to the growth stimulation distributed over a large area.

The arrangement of the pins and/or the geometry of the pins is/are selected to be different in different regions of the fastening side of the implant. The arrangement of the pins is in this connection to be understood as the position of the pins relative to one another on the fastening side, that is, for example, the spacing of the pins from one another and the number of the pins per unit of area of the fastening side of the implant. The geometry of the pins is here to be understood, in the widest sense, as both the length and the cross-sectional surface, the shape of the cross-section and the design of the pins in their longitudinal extent. The geometry of the pins is preferably selected such that they can be introduced as such into the bone without any predrilling of the bone. On the penetration into the bone tissue, the pins displace bone tissue and are held thereby. The total bone tissue consists of bony tissue and a medullary portion. For reasons of simplicity, the medullary portion of the bone will here, and in the following, also be subsumed under the bone tissue even though it is per se not entirely accurate to call the medullary portion of the bone tissue. The bony tissue includes cortical bone tissue and spongious bone tissue. The components of the bone combined here as bony tissue have a structure, unlike the medulla, and are therefore able to transmit a force. Both the strength of the anchorage of the anchorage pins in the bone and the force required for the introduction of the anchorage pins into the bone substantially depend on how much bony tissue, that is cortical bone tissue and, at the resection surface of a bone, in particular spongious bone tissue, is displaced by an anchorage pin. In the implant described here, the length of the anchorage pins and/or the cross-sectional area of the anchorage pins per unit of area of the fastening side is therefore selected differently in dependence on the density of the bone opposite which a surface segment of the implant is provided, that is in dependence on the proportion of the bony tissue in the total tissue. For example, in regions of a relatively lower proportion of bony tissue in the total tissue, the anchorage pins are selected to be longer and/or anchorage pins having a larger cross-sectional surface are selected and/or anchorage pins of a different cross-sectional shape are selected and/or more pins are arranged per unit of area of the fastening side. Seen in total, the volume of the anchorage pints per unit of area of the fastening side of the implant is therefore selected to be the larger, the smaller the proportion of the bony tissue in the total bone tissue is. The geometry and/or the arrangement of the pins is accordingly selected corresponding to the proportion of bony tissue in the total tissue of the bone material opposite which the region of the fastening side is provided such that in total less tissue, that is bony tissue and medulla, is displaced in regions of a relatively high proportion of bony tissue than in regions of a relatively lower proportion of bony tissue. In an embodiment of an implant, the geometry and/or the arrangement of the anchorage pins is selected such that the volume of the anchorage pins per unit of area of the fastening side behaves substantially inversely proportionally to the proportion of bony tissue in the total tissue of the bone opposite which the implant is provided. Substantially the same amount of bony tissue per unit of area of the fastening side of the implant is thereby displaced at each point in the bone opposite which the implant is provided. The introduction of force of the anchorage pins is thus distributed evenly over the force transmitting structured bone components such that again in total more bony tissue is used for the force transmission in regions of a lower proportion of bony tissue. In regions in which proportionally less bony tissue is present, in which in other words the bone substance is less resistant, the introduction of force is accordingly distributed over a larger volume and the local load on the tissue is thus reduced.

In an embodiment of the implant, the anchorage pins are arranged such that they only, or substantially only, penetrate into the spongiosa on implantation and thus receive a primary fixation by displacement of the trabeculae, whereas an ongrowth of bone tissue at the pins takes place after a certain time. In this embodiment, no pin-like anchorage elements, or only comparatively short anchorage elements, i.e. at most a few mm long, for example up to 2 to 3 or 5 mm, are provided in the region of the cortical bone.

In an embodiment of an implant of the described kind, the geometry and/or the arrangement of the anchorage pins is/are also selected in dependence on the orientation of the trabeculae in addition to the dependence on the proportion of the bony tissue in the total bone tissue in the region of the implant which is provided for arrangement on a spongious region of the resection area. In a further embodiment, the anchorage pins are only arranged in regions of the implant which are provided on a spongious region of the resection area, whereas no pins, or at most very short pins, actually tips, are arranged in the region provided for arrangement on the cortex. In this respect, an embodiment of the implant is characterized in that the length of the anchorage pins and/or the number of the anchorage pins per unit of area of the fastening side of the implant and/or the cross-sectional surface of the individual anchorage elements increase from the rim of the fastening side of the implant toward the center of the surfaces.

Pins can, for example, be considered as anchorage pins which have a constant cross-section over their total longitudinal extent, in particular cylindrical pins, pins which reduce in their cross-sectional areas towards the tip, in particular conical pins, as well as pins whose longitudinal extents have regions of constant cross-section as well as regions of variable cross-section. Pins which have a converging cross-section have a half angle in this region which amounts to a maximum of 5°, 4°, 3° or 2°. The angle is, for example, small enough to ensure an at least approximately self-locking seat of the anchorage pin in the bone material. The geometry of the cross-section of the anchorage pins is, for example, circular, but can easily also be a polygon, in particular triangular or rectangular, or can have a cruciform shape or a star shape, or can also be a hollow section, with this design easily being able to differ in the anchorage pins which are arranged in different regions of the fastening side of an implant or in different anchorage pins. The size of the cross-section of the anchorage pins can then be given by a diameter of a circle circumscribed at the pin cross-section at the base of the pin and is, for example, in the range of 0.5 millimeters to 3 millimeters.

An embodiment of the implant is characterized in that the anchorage pins vary with respect to their length and/or with respect to the number of pins per unit of area of the fastening side and/or with respect to their cross-sectional area.

In another embodiment, at least two anchorage pins are connected to one another at the ends of the anchorage pins adjacent to the implant by a wall-like structure which extends, on the one hand, from one anchorage pin to the other anchorage pin and, on the other hand, extends by a vertical extent from the fastening side to the remote end of the anchorage pins, with the vertical extent being smaller than the length of the anchorage pins and with the vertical extent of the wall-like structure amounting to between 1 mm and 4 mm in a more specific embodiment. This arrangement inter alia improves the security of the pins as required against kinking on the implantation, which is important for the reason that the pins are preferably pressed into the bone without predrilling.

Furthermore, an implant is characterized in that the fastening is effected by the totality of the pins which are arranged in the manner of a bed of nails. In this connection, in an embodiment, the spacings (s) between the longitudinal axes of the anchorage pins amount to at least 1 mm, in particular 1.5 mm and furthermore at least 2 mm and no more than 10 mm, in particular no more than 5 mm and furthermore no more than 3 mm. In this connection, the surface density of the anchorage pins amounts, for example, at a minimum to around 1 pin/cm$^2$ and at a maximum to 30/cm$^2$, for example at least 3/cm$^2$. Furthermore, in an exemplary embodiment of the implant, the anchorage pins are arranged at least regionally on an equidistant grid, in particular on a base grid of equilateral triangles.

In an embodiment, at least one anchorage pin has a section diverging toward the fastening side of the implant, with the half angle ($\alpha$) of the divergence amounting to a maximum of 5°, 4°, 3° or 2°. Such an acute cone on the one hand facilitates the introduction of the anchorage pins into the bone, on the one hand, and ensures a good and reliable stability of the pins, on the other hand.

For example, an implant is characterized in that the cross-sections of the anchorage pins have circumscribed circles whose diameters at the base of the pins, i.e. at the end facing the fastening side of the implant, amount to a least 0.5 mm, and in particular to at least 1 mm. Furthermore, these diameters at the base of the pins amount in an exemplary embodiment to at most 3 mm, in particular at most 2 mm and furthermore in particular at most 1 mm. The length of a longest anchorage pin of the anchorage pins, for example, amounts to a minimum of 8 mm, in particular a minimum of 15 mm or a minimum of 20 mm and in an embodiment to a minimum of 25 mm. In a further embodiment, the length of the anchorage pins generally amounts to a minimum of 2 mm, in particular to a minimum of 3 mm or to a minimum of 5 mm and in an embodiment to a minimum of 10 mm. The maximum length of the anchorage pins in an embodiment of the implant is a maximum of 50 mm, in particular a maximum of 35 mm and in a special embodiment a maximum of 25 mm. In an embodiment, an implant has at least one anchorage pin having a length of at least 15 mm and in particular of at least 25 mm.

The anchorage pins furthermore in particular have length/diameter ratios of at least 3, with at least some anchorage pins having length/diameter ratios of at least 8 and in particular of at least 10 or 12 in a further development.

The longitudinal axes of the anchorage pins are in particular arranged substantially parallel to one another and furthermore substantially perpendicular to a resection surface associated with the implant.

Generally, an implant of the kind proposed here is in particular especially advantageous when it is provided for the implantation on a bone region with comparatively poor bone quality which distributes the force transmission over a large area and an adaptation of the density of the force flow to the local bone quality takes place.

Further criteria for the design of the geometry of the anchorage pins and their arrangement on the fastening side of the implant result from the dependent claims and the embodiments.

In a further development of the implant, at least one guide element and/or centering element is arranged on the fastening side and in particular extends further away from the fastening side than the longest anchorage pin. On the placement of the implant, the guide element and/or centering element is introduced into a predrilled opening of the bone and thus defines the position of the implant on the bone before the actual anchorage of the implant by means of the anchorage pins. In another further development of the implant, the implant has two such guide elements and/or centering elements. They then define the position and the orientation of the implant on the bone before the pins penetrate into the bone and fix the implant.

An embodiment of the implant described above is a proximal tibial implant, in particular a tibial plateau, such as is used for knee joint prostheses.

A further embodiment is a distal femoral component of a knee joint prosthesis. It can be a monocondylar or a bicondylar femoral component.

Another embodiment is a proximal femoral component for a hip joint in particular a cap for arrangement on the femoral head such as is used for so-called "resurfacing". In an embodiment, the proximal femoral component has a metallic articulation surface which, for example, has a shape error of less than 10 μm or even less than 2 μm. Such a proximal femoral component is, for example, suitable for use with a metal-to metal slide pairing in a hip joint prosthesis.

The described implant is naturally also suitable as an acetabulum component of a hip joint prosthesis.

Equally, the implant can be used as a component of a shoulder joint prosthesis which is fastened to the scapula or to the humerus by means of the anchorage pins.

Another embodiment relates to an intervertebral implant which is anchored in the vertebral bodies by means of the anchorage pins.

This list cannot and does not want to be exclusive.

An embodiment of the implant is characterized in that comparatively densely adjacent anchorage pins are provided substantially over the total surface provided opposite the resection surface of a bone and in particular the spongious region of the resection surface and their spacing from one another amounts to a few mm, for example to 3 mm or to 5 mm.

The anchorage pins ensure a good primary fixation of the implant in the bone due to static friction of the displaced bone volume at the plurality of pins. The primary fixation achieved in this manner is the larger, the steeper the sides of the pins are. If, however, the pins have a pronounced conical shape which is enlarged toward the base of the pins at a comparatively large divergence angle, the stability is lower and the implant can be removed more easily for any required following interventions. The pins can equally be made with different surface properties to influence the secondary fixation by the ongrowth of bone. Generally, the secondary anchorage will be more pronounced with a rough surface than with comparatively smooth surfaces. A coating with hydroxilapatite or the like is also possible. The pins are, for example, made from titanium.

The features of implants of the kind described here and described above and in the claims can naturally also be combined among one another.

An implant of the kind described above is suitable for the implantation using bone cement and also for cement-free implantation.

Figure 1B:
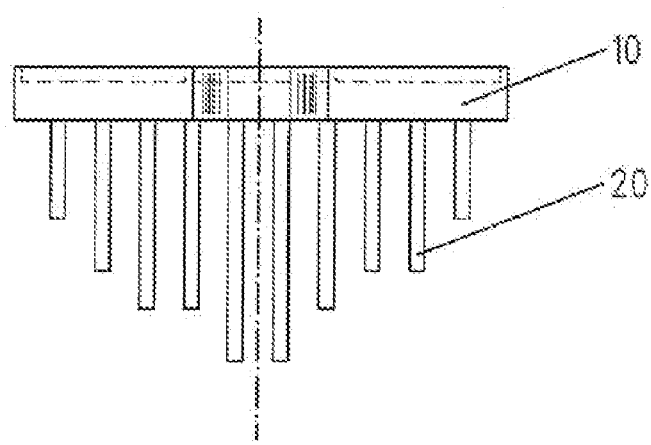
Figure 1C:
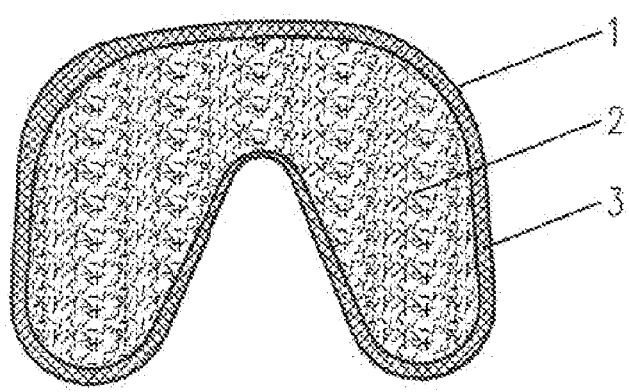
Figure 2A:
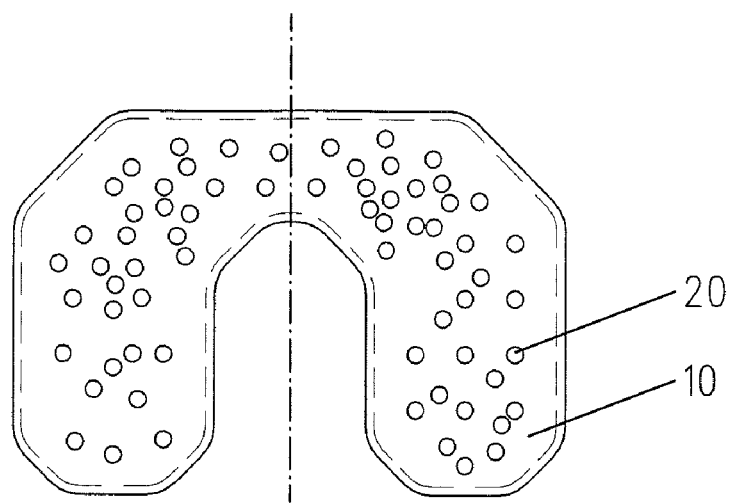
Figure 3:
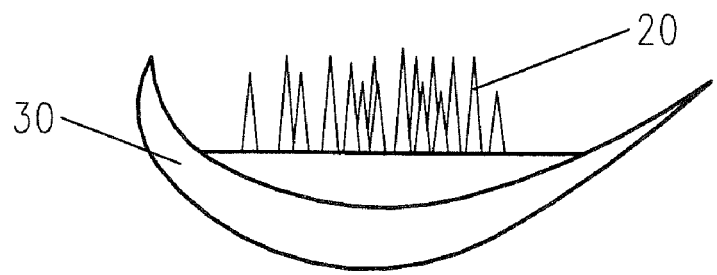
Figure 5:
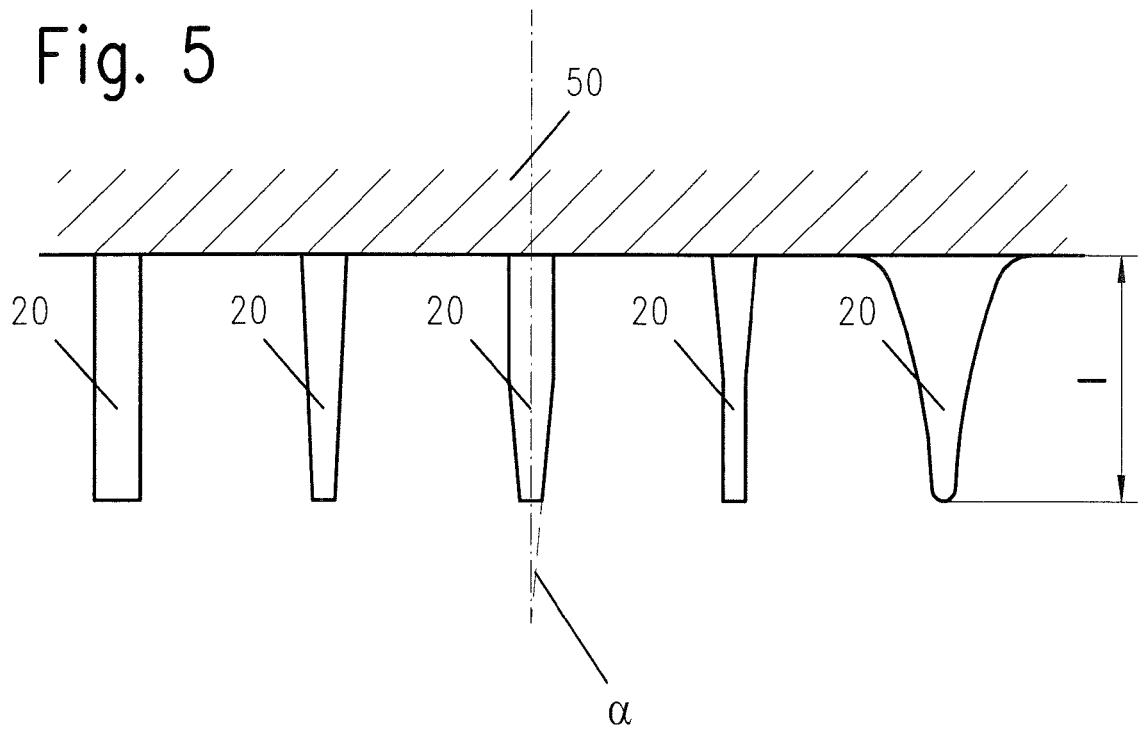
Figure 6:
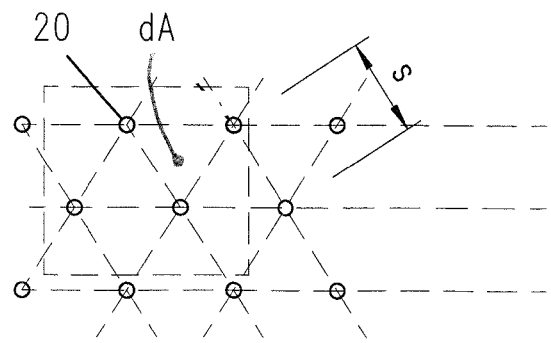
Figure 7:
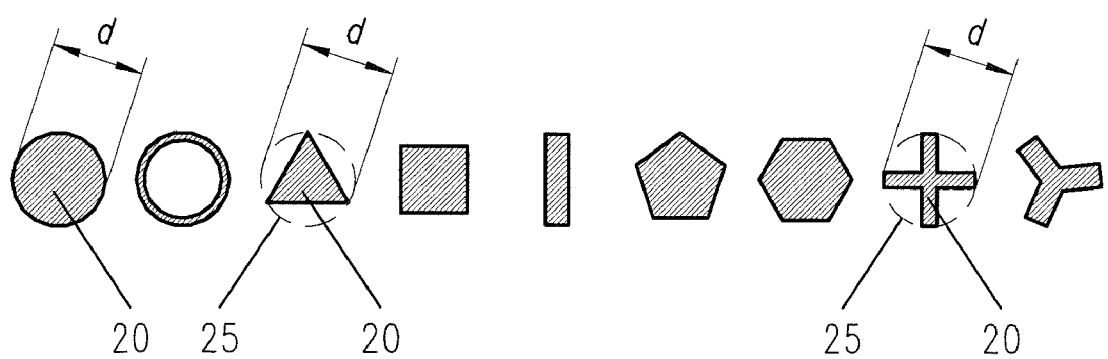
Figure 8:
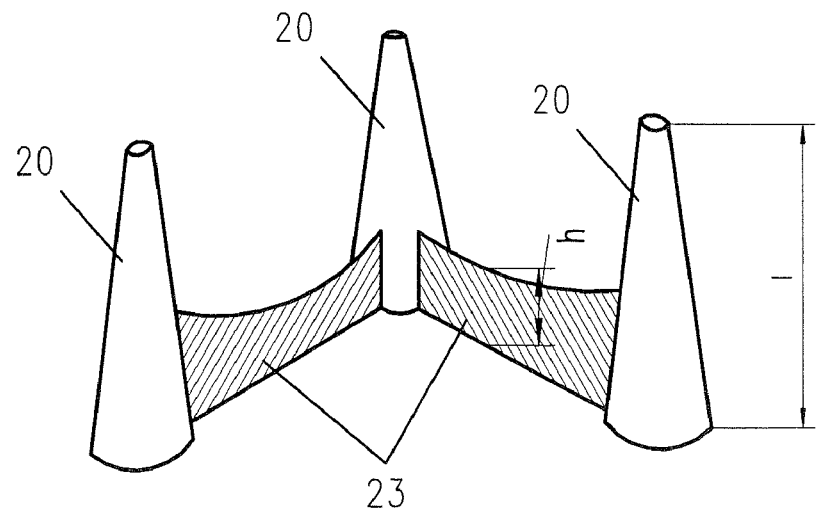
Figure 9A:
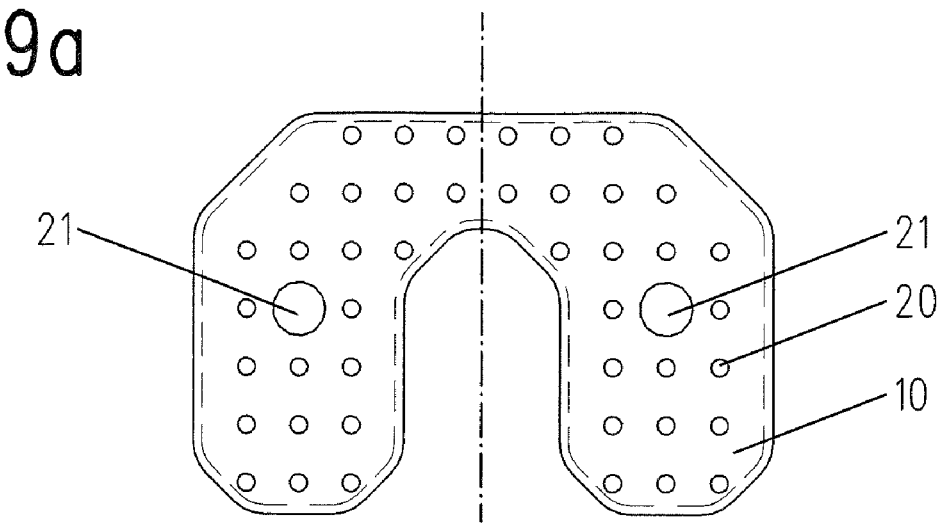
Figure 9B:
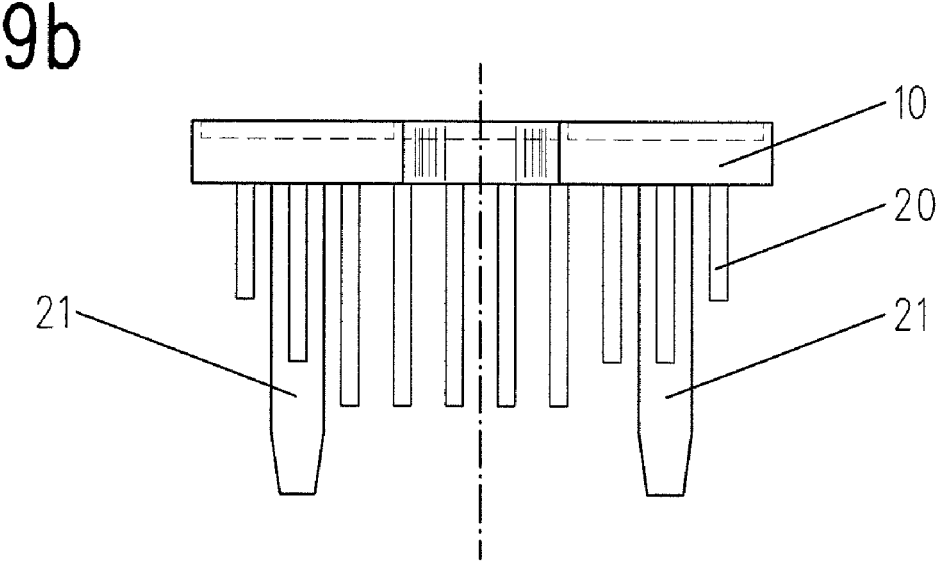
Figure 10:
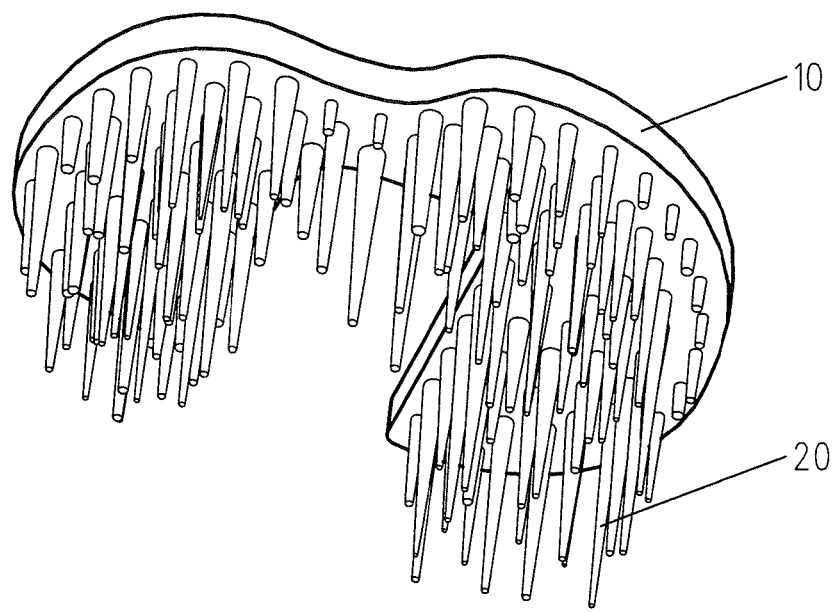
Figure 10:
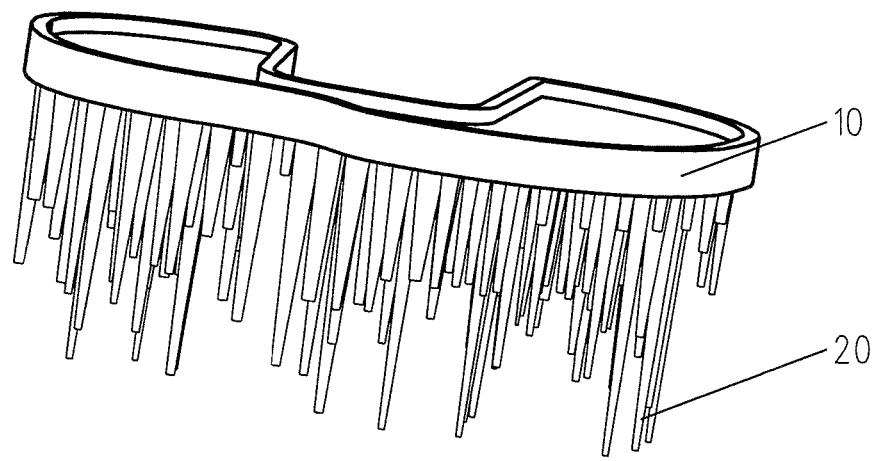
Figure 10:
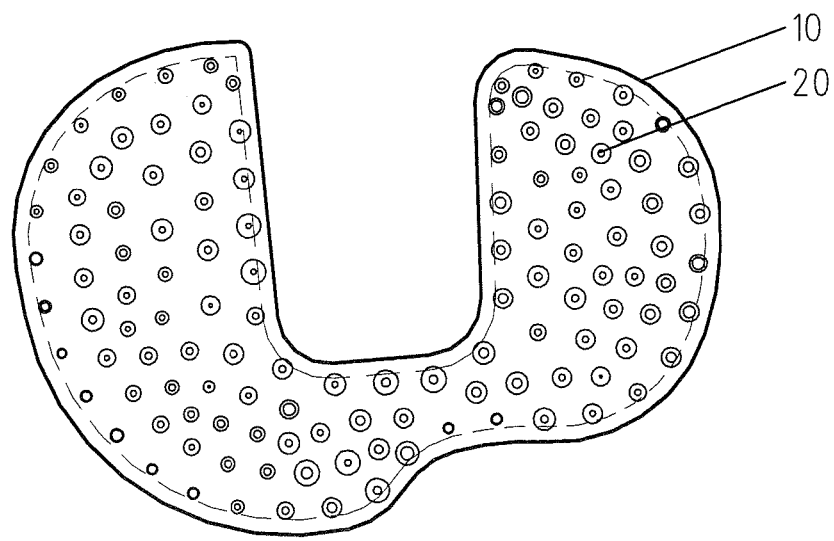
Figure 11:
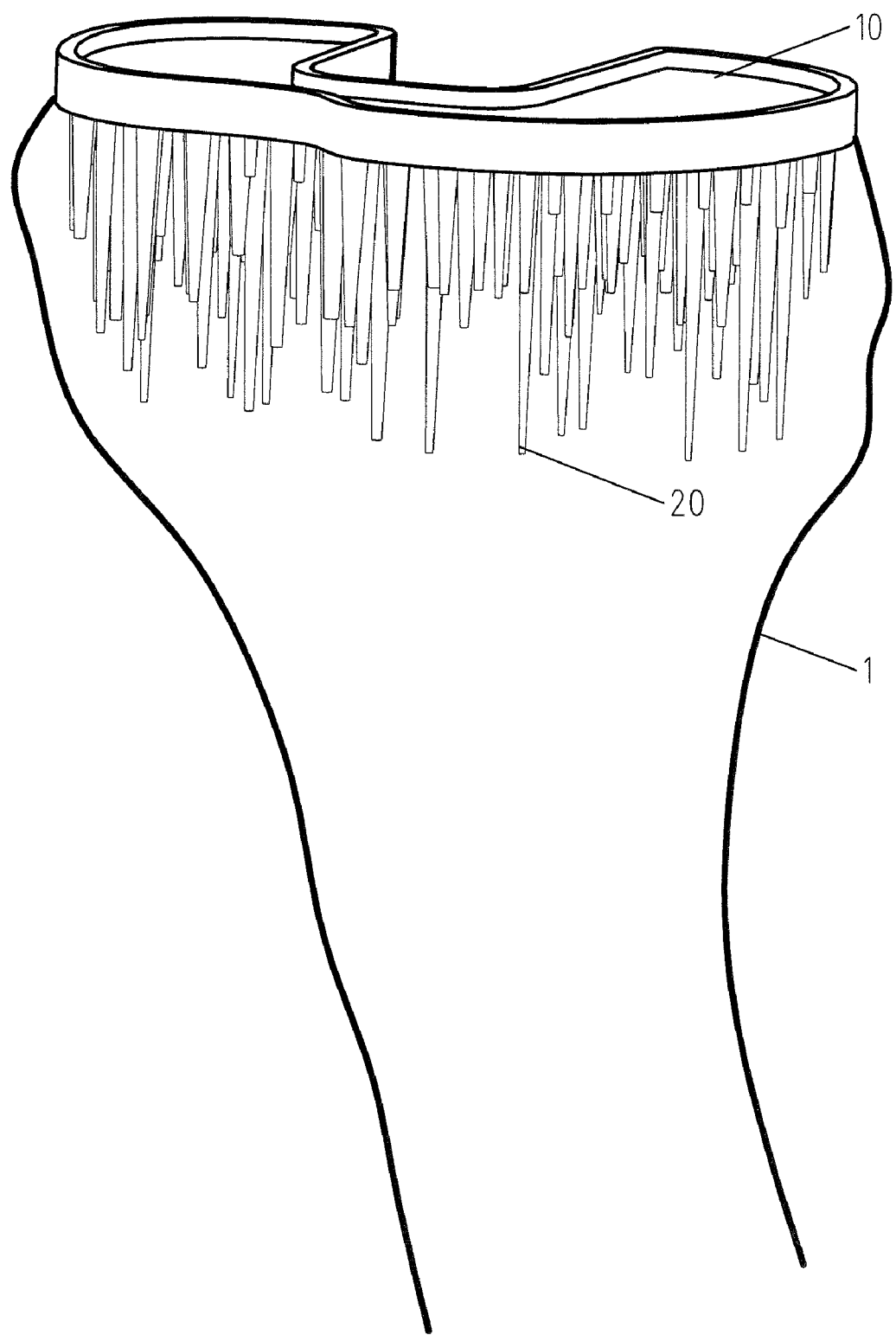
Figure 12:
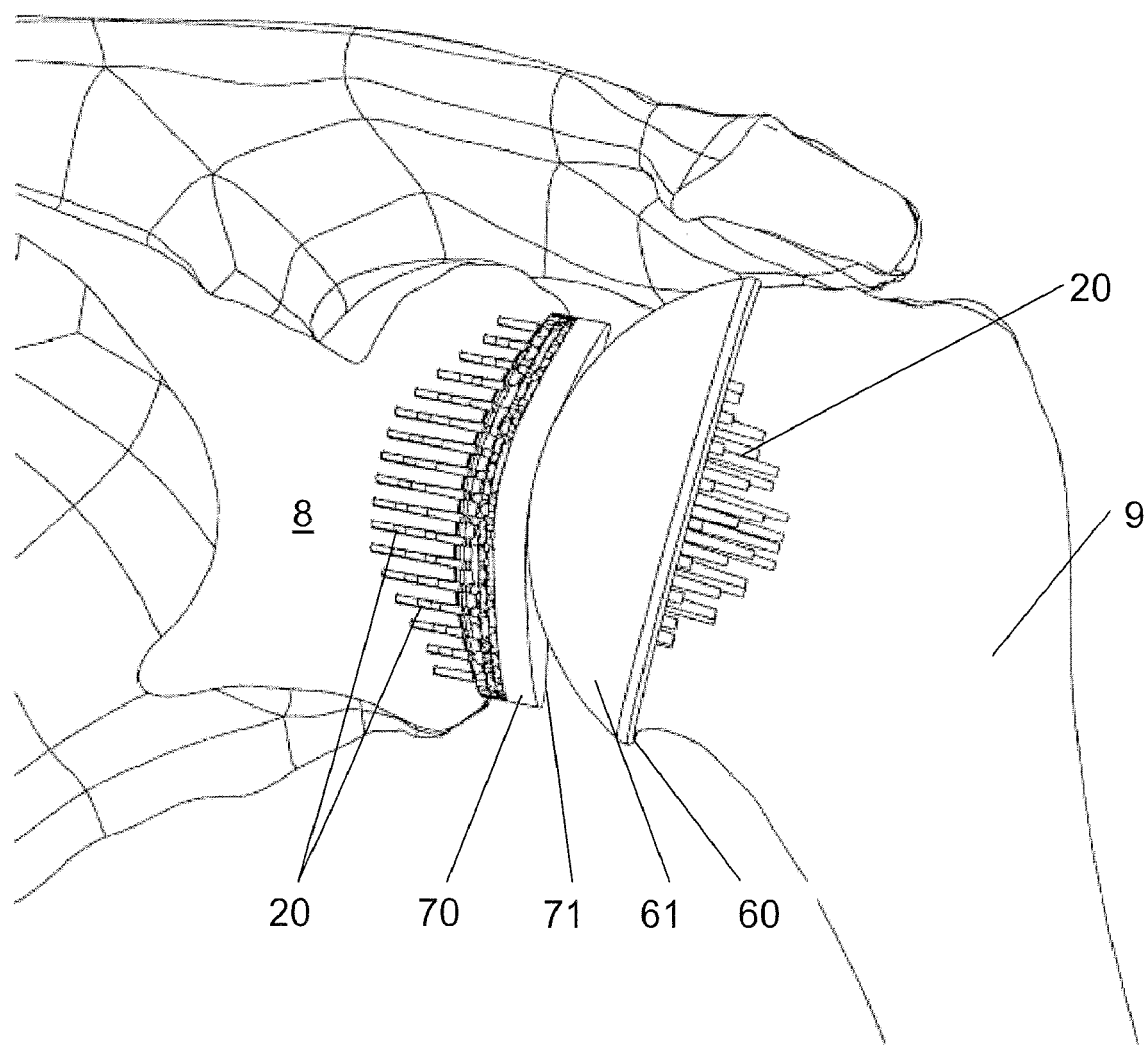
Figure 13:
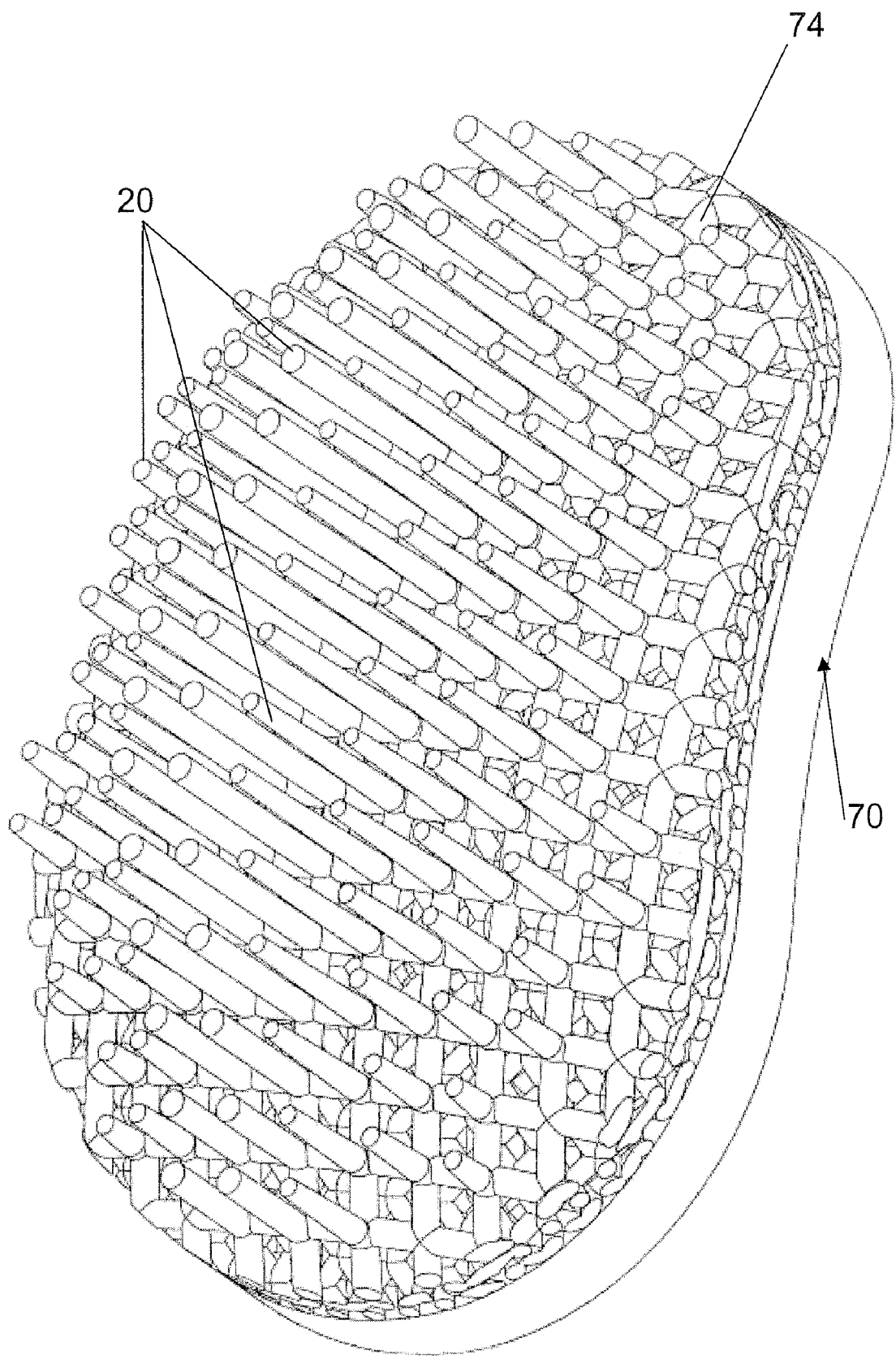
Figure 14:
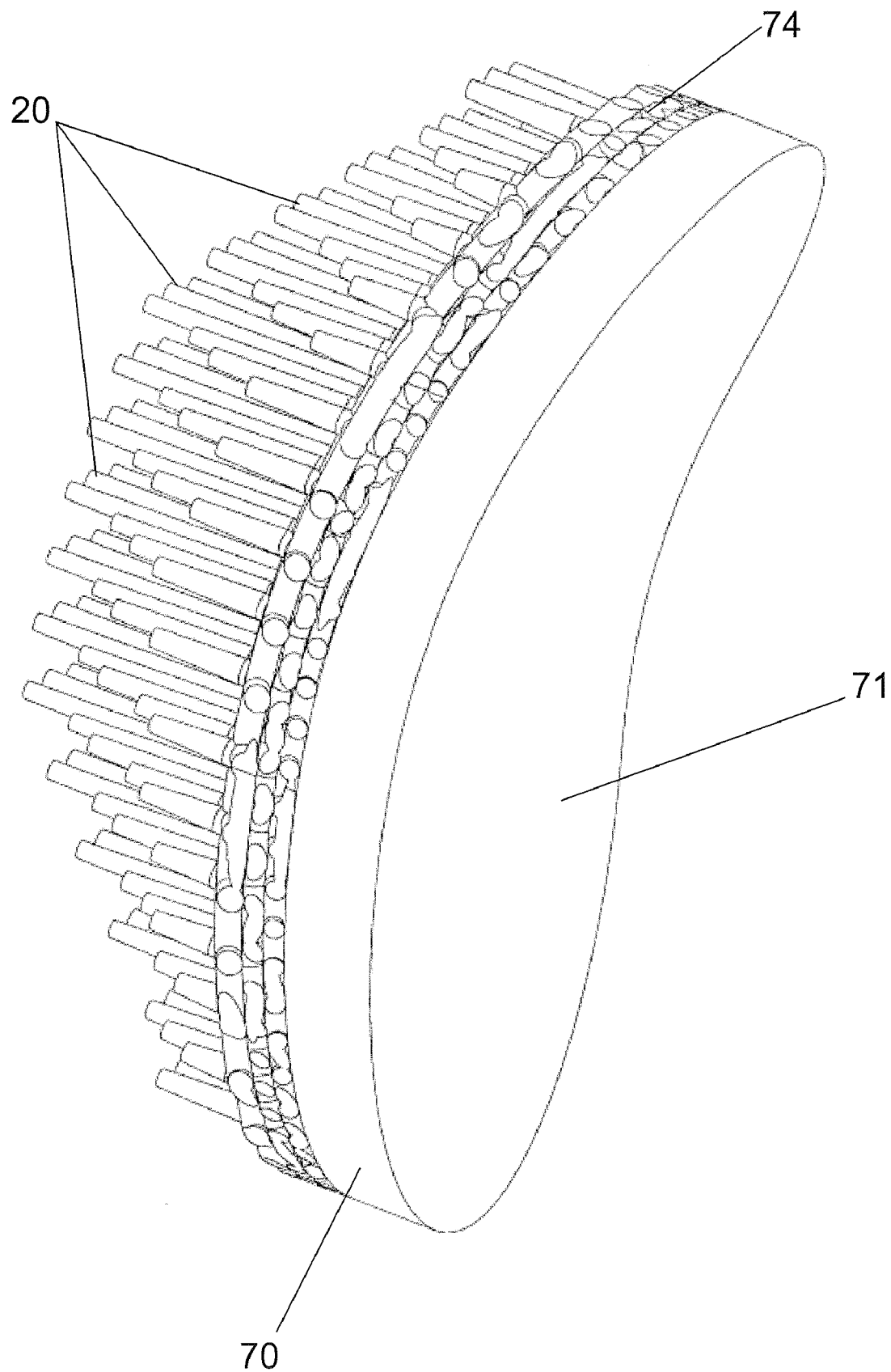

The implant described above will be described in more detail in the following with reference to embodiments shown in the drawing. There are shown in detail FIG. 1 a schematic representation of a tibial implant of the described kind as well as a plan view of a resection surface of a tibia, with the implant being provided for arrangement thereon;

FIG. 2 a further embodiment of the implant from FIG. 1;

FIG. 3 a side view of a femoral component of a knee joint prosthesis in the described and claimed manner;

FIG. 4 a schematic representation of a femoral head prosthesis as well as of a femur prepared for implantation;

FIG. 5 various exemplary geometries of anchorage pins;

FIG. 6 an example for the arrangement of pins on a grid;

FIG. 7 various exemplary pin cross-sections;

FIG. 8 an embodiment of an arrangement of anchorage pins;

FIG. 9 a further embodiment of a tibial implant as well as a plan view of a prepared tibia;

FIG. 10 a further example of a tibial implant;

FIG. 11 a tibial implant from FIG. 10 in the implanted state;

FIG. 12 a shoulder implant in which the humerus component and also the glenoid component are anchored in the described manner;

FIG. 13 a first view of the glenoid component of FIG. 12;

FIG. 14 a second view of the glenoid component of FIG. 12; and

Figure 15:
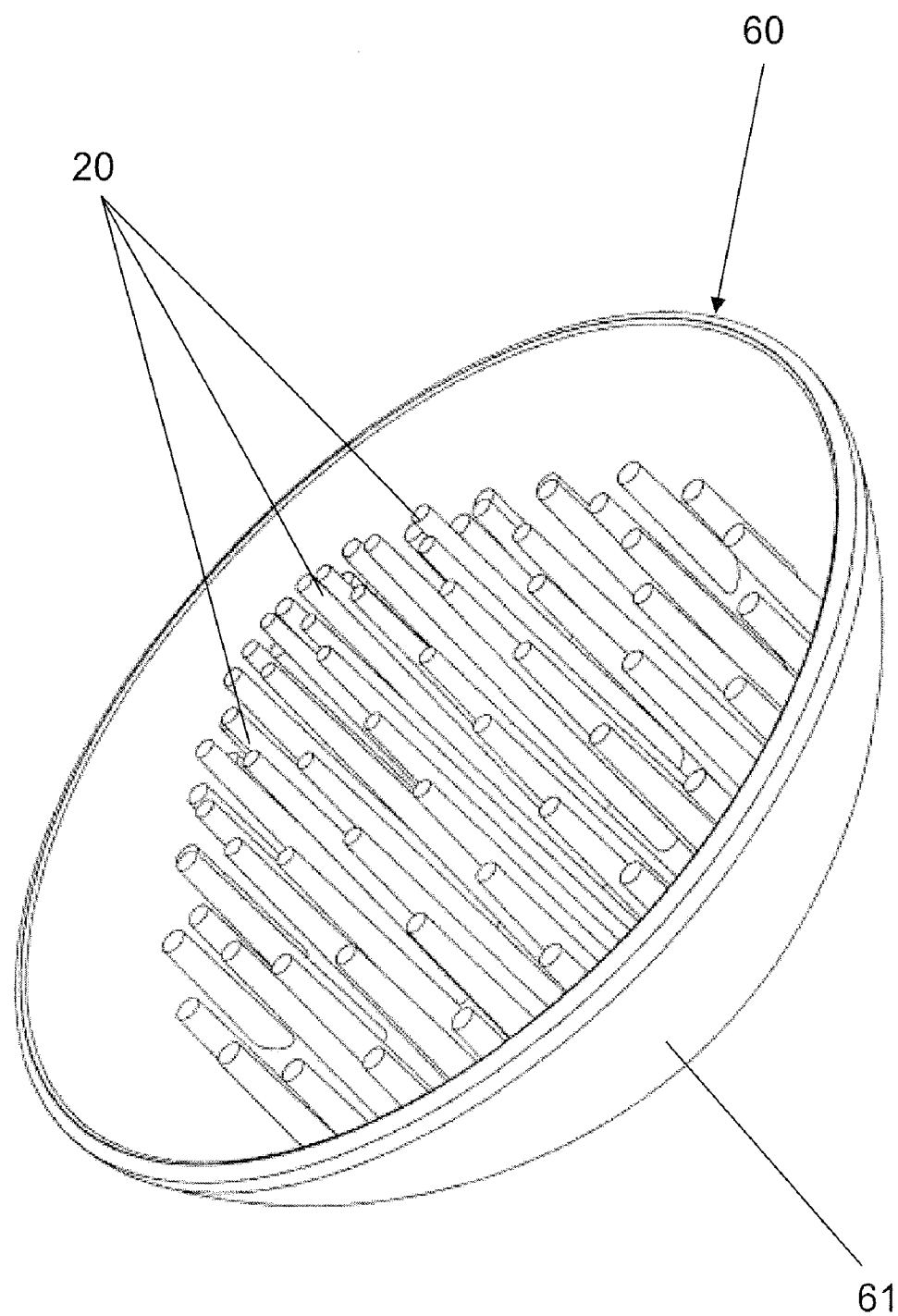

FIG. 15 the humerus component of FIG. 12.

The embodiments serve for the better understanding of the invention and should not be used for a restriction of the invention described in the claims.

In FIG. 1, a tibial plateau 10 is shown in a very simplified representation and is made in the proposed manner. FIG. 1a shows a plan view of the fastening side with which the implant is provided for contact with the resection surface of the bone. Anchorage pins 20 are arranged on the fastening side of the tibial plateau 10. They are arranged on a square grid in this Figure, but this is in no way compulsory; any other desired arrangement patterns appropriate for the application are also possible. FIG. 1b shows a view along the line marked by B-B in FIG. 1a. FIG. 1c shows a plan view of the resection surface of a tibia 1. The cortex 3 at the rim of the resection surface substantially comprises solid bone tissue and is only slightly deformable and is comparatively brittle. In the region of the spongiosa 2, the bone tissue is, as already described above, composed of bony tissue and medulla and has a greater deformability. As indicated by the differently dense hatching, the proportion of bony tissue in the total tissue is different in different regions of the resection surface. In the example shown here, the proportion of the bony tissue reduces from the cortex toward the center, whereby the strength also reduces and the deformability of the bone increases. It can be recognized with respect to FIG. 1b that the length of the anchorage pins is adapted to this circumstance and is larger in the regions provided for arrangement in regions of the bone with a low proportion of bony tissue than in regions of a high proportion of bony tissue. In this example, all the anchorage pins are shown as cylindrical pins having a constant cross-sectional surface. The pins can naturally also be conical in total or regionally or can, for example, converge acutely at the front end remote from the implant. It is equally not compulsory that all the pins have the same cross-sectional shape or longitudinal contour.

Figure 2B:
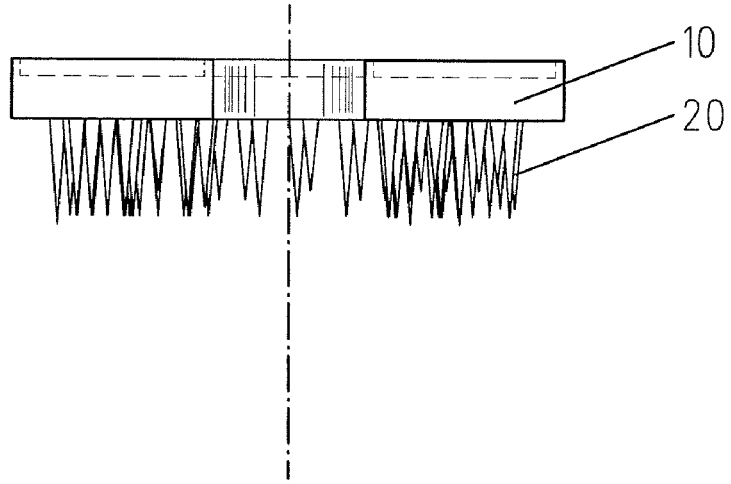

FIG. 2 shows an alternative embodiment of such a tibial plateau. The anchorage pins 20 on the tibial plateau 10 are arranged in a variable density over the surface of the fastening side of the implant. As can be recognized from FIG. 2b, the anchorage pins 20 are almost of equal length and converge acutely. An equivalent effect as is adopted in FIG. 1 due to the longer anchorage pins is achieved by the reduction of the spacing between the anchorage pins in the regions of the implant which are provided for arrangement on regions of a resection surface with a lower proportion of bony material. Anchorage pins of different lengths and other and/or different shapes can naturally also be used in the embodiment shown in FIG. 2.

A condyle implant 30 is shown schematically in FIG. 3 which has anchorage pins 20 of different lengths for anchorage at the resection surface of a bone.

Figure 4A:
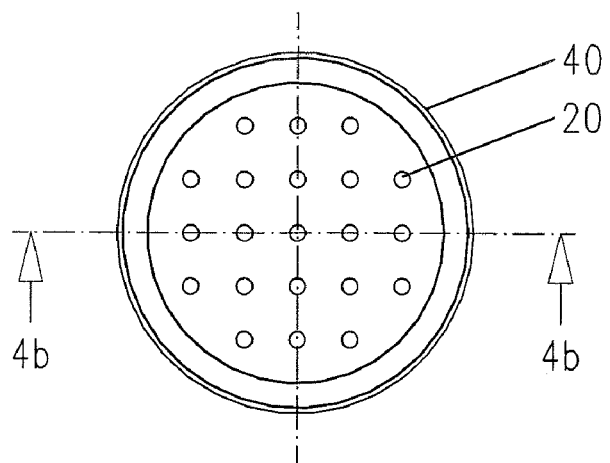
Figure 4B:
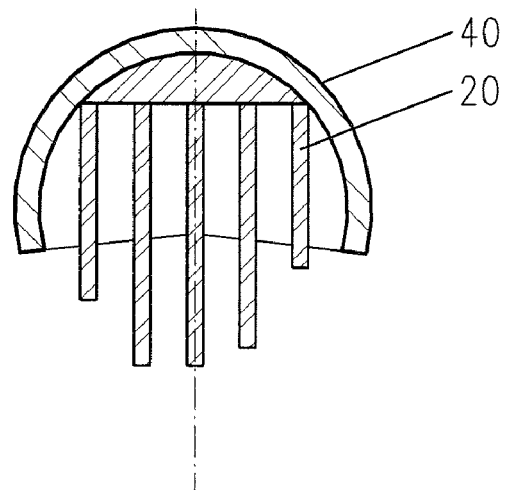
Figure 4C:
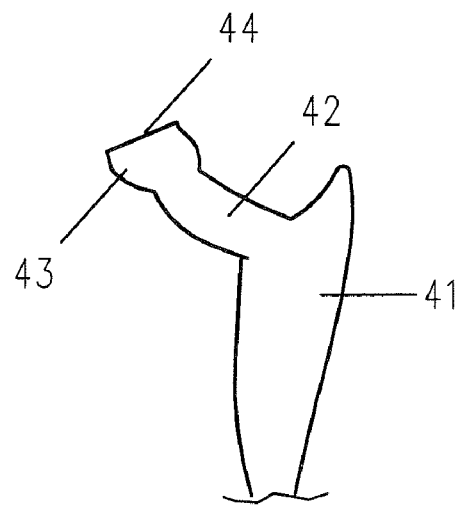

The use of an implant of the kind described here at the femoral component of a hip joint prosthesis is shown in FIG. 4. A femoral cap is shown in FIGS. 4a and 4b as is used for the so-called resurfacing of a femoral head. FIG. 4b is a sectional view of the femoral cap as illustrated in FIG. 4a taken along line 4b-4b of FIG. 4a. The "resurfacing" is characterized in that as little bone as possible is removed and substantially only the cartilage of the natural articulation surface is replaced by an artificial articulation surface. The articulation surface of the femoral cap 40 preferably consists of metal, in particular of a steel having a high carbon proportion, which is, however, not material to the invention here. The femur 41 is shown schematically in FIG. 4c with the femoral neck 42, the femoral head 43 and the resection surface 44 at the femoral head. The proportion of the bony tissue in the total bone tissue is also different over this resection surface. For example, cortex is located at the outer rim of the resection surface into which anchorage pins can only be introduced with difficulty and with the risk also being present of causing a splintering of the cortex with non-predrilled holes for the introduction of the pins. In contrast, spongious material having a large medulla proportion is located at the center of the resection surface. The anchorage pins 20 of the femoral cap 40 are therefore selected differently in different regions adapted to the bone density and are longer at the center than at the rim, whereas at the far rim, in regions which come to lie on the cortex, no anchorage pins are arranged. The fastening of an implant described here by means of a collective of pins adapted to the local bone structure and bone strength can naturally also be used in the fastening of the associated acetabulum component.

A plurality of possible embodiments of anchorage pins 20 are shown schematically in FIG. 5. They extend with a length I starting from the implant 50. Some of the exemplary anchorage pins 20 have divergent regions seen from the tip toward the implant. The half angle of the divergence is marked by α. This angle is for example 2°, 3°, 4° or 5°. Small angles, corresponding to very acute pins, facilitate the introduction which in particular takes place into a non-predrilled bone and improve the security of the seat of the pins in the bone. Pins with larger divergence angles, in contrast, have a greater security against kinking on the introduction and facilitate the explantation in any required revisions.

FIG. 6 illustrates further geometrical connections of the arrangement of anchorage pins on the fastening side of an implant. In this example, the anchorage pins 20 are arranged on a grid of equilateral triangles. The spacings between the central longitudinal axes of two adjacent anchorage pins are marked by s. The density of the anchorage pins is the number of pins within a surface element dA and is specified, for example, as the number of pins with respect to a unit of area of, for example, 1 cm².

FIG. 7 illustrates different cross-sectional shapes of anchorage pins. Furthermore, in some of these exemplary anchorage pins, the circumscribed circle 25 is shown with the diameter d.

FIG. 8 illustrates a further embodiment in which wall-like structures 23 whose height h is smaller than the length I of the anchorage pins 20 are arranged between anchorage pins 20, with the height within such a wall-like structure also being able to be variable, for example such that the height of the wall-like structure is larger adjacent to the anchorage pins than at the center between two anchorage pins; wall-like structures of constant height are naturally also possible or those in which the height is larger at the center between two anchorage pins than adjacent to the anchorage pins. The vertical extent of the wall-like structure amounts, for example, to between one millimeter and four millimeters and should be limited such that not too may blood vessels are cut by these wall-like structures within the bone.

Figure 9C:
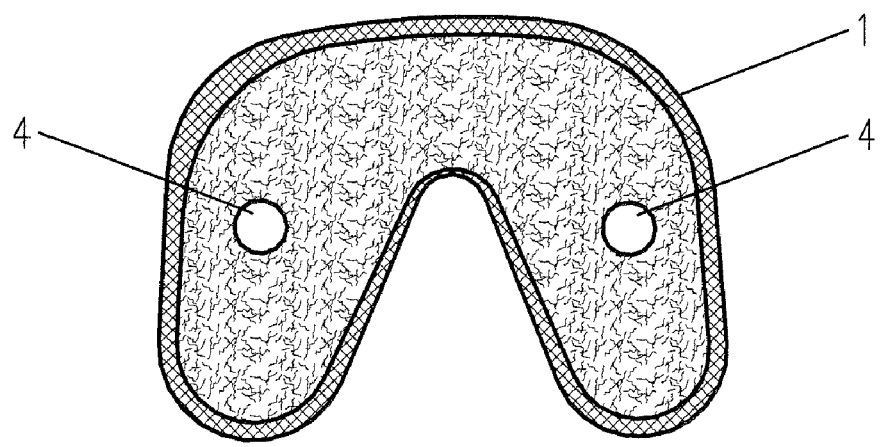

FIG. 9 shows a modification of the tibial plateau of FIG. 1. On the fastening side, the tibial plateau 10 has, in addition to the anchorage pins 20, guide elements 21 which project further from the fastening side than the longest anchorage pin. Two positioning bores 4 are introduced into the resection surface of the tibia shown in FIG. 9c and their spacing corresponds to the spacing of the guide elements 21. On the placement of the tibial plateau onto the resection surface, the guide elements 21 first penetrate into the bores 4 of the tibia and position the tibial plateau there with respect to position and direction before the implant is fixed in the bone by pressing or hammering the anchorage pins into the bone tissue. The guide elements 21 have a conical tip region in addition to the cylindrical guide region for the easier introduction into the bores 4. For the best possible function, the cylindrical guide region of the guide elements is longer than the longest anchorage pin such that the position and direction of the implant are already securely fixed before the penetration of the anchorage pins.

FIG. 10 shows an exemplary tibial plateau 10 in which the arrangement and geometry of the anchorage pins 20 of the complex bone density distribution is adapted to a real resection surface of a tibia. FIG. 11 shows this tibial plateau on a tibia 1 in the implanted state.

A shoulder prosthesis is shown in FIG. 12 in which the components are designed in the manner described and claimed. A cap 60, which is made, for example, from a metallic material and has an articulation surface 61 is anchored in the humerus 9 by means of anchorage pins 20 of different length. The application of such a cap as a joint surface replacement is likewise actually a "resurfacing" in the manner explained in connection with FIG. 4. A glenoid component 70 having an articulation surface 71 is likewise anchored in the scapula 8 by means of a plurality of anchorage pins 20 arranged in a pin field. The surgeon frequently finds very poor bone quality at these points which makes a secure primary fixation of the implants more difficult. The distribution of the anchorage over the plurality of pins which are shaped and arranged such that the force is distributed over a bone volume which is the larger, the smaller the local density and stability, of the bone is, has a very advantageous effect. Due to the high porosity of the bone which is often found at the implantation sites, the implantation by pressing in or hammering in the implants is facilitated, whereas the distribution of the holding forces over a number of pins facilitates the primary fixation. A large surface of the pins 20 is available for a secondary fixation by ongrowth on the bone. The strength of the hold and the intensity of the connection to the bone can be influenced in a manner known per se by the geometry of the pins as described above and their surface properties, in particular their roughness. The glenoid component is shown enlarged in FIGS. 13 and 14. In this example, it comprises, in addition to the anchorage pins 20, an articulation surface 71 which is made, for example, of polyethylene, in particular of a highly cross-linked and/or a high-molecular polyethylene, as well as a multilayer wire mesh 74 which is made, for example, of titanium and is known, for example, under the name "Sulmesh". This is very suitable for the anchorage of the polyethylene articulation surface and likewise promotes an ongrowth of the bone. FIG. 15 shows the humerus component which has the shape of a hollow sphere 60 here and in whose interior the anchorage pins 20 are arranged. The pins are longer at the center of the anchorage surface than at its rim both in the glenoid component 70 and in the humerus component 60.

The embodiments described above only represent some selected examples from the possibilities which are available to the skilled person. Further embodiments of the invention easily become clear to the skilled person in light of these embodiments.

The implantation of the implants described here takes place in that the corresponding bone is cut. The anchorage pins are pressed into the bone structure of the arising resection surface without corresponding holes having been predrilled. On the use of implants having centering spigots and/or guide spigots, such as is shown in FIG. 9, bores are introduced for the reception of the spigots and the bone; no bores are introduced for the reception of the spigots and the bone. The friction of the pins in the bone tissue and the large number of pins, as well as their fitting—whether due to the arrangement or to the geometry—to the local bone density ensure a good primary anchoring of the implant in the bone so that the implantation can take place free of cement; it is naturally also possible additionally to fix the implant on the resection surface with bone cement.

When an implant is provided, as shown in FIG. 9, with guide elements and/or centering elements, corresponding guide bores and/or centering bores have to be introduced into the resection surface, in particular by means of a suitable gauge. They are dimensioned, for example, such that they can receive the guide elements and/or centering elements with as little clearance as possible. On the implantation, the guide elements and/or centering elements are then first introduced into the associated bores of the resection surface, whereby the position and/or direction of the implant on the resection surface are defined and the implant is then pressed in or hammered in using the anchorage pins for which no holes were predrilled.

REFERENCE NUMERAL LIST

1 bone
2 spongiosa
3 cortex
4 bore
8 scapula
9 humerus
10 implant, tibial plateau
20 anchorage pin
21 guide spigot and/or centering spigot
23 areal connection structure, wall-like structure
25 circumscribed circle of an anchorage pin
30 distal femoral component
40 femoral cap
41 femur
42 femoral neck
43 femoral head
44 resection surface
50 implant
60 humerus implant
61 articulation surface of the humerus implant
70 glenoid implant
71 articulation surface of the glenoid implant
74 wire mesh structure
d thickness of an anchorage pin, diameter of the circumscribed circle of an anchorage pin
dA surface element
l length of an anchorage pin
H height of the wall-like structure
S spacing of two anchorage pins
α angle

The invention claimed is:

1. An implant for anchorage to a bone, wherein bony tissue comprises at least a portion of the total tissue of the bone, the implant comprising:
a fastening side for arrangement adjacent to the bone; and
a plurality of anchorage pins arranged on the fastening side and together extending away from the fastening side in essentially the same longitudinal direction, wherein the anchorage pins anchor the implant in the bone, with at least one of a pin arrangement and a geometry of the plurality of anchorage pins being different in different regions of the fastening side of the implant and the volume of the anchorage pins per unit of area of the fastening side of the implant being different in different regions of the fastening side, with at least one of the pin arrangement and the geometry of the plurality of anchorage pins selected in accordance with the proportion of bony tissue to the total tissue of the bone opposite to which the fastening side is provided for implantation such that upon implantation a lower volume of tissue per unit of area of the fastening side of the implant will be displaced by the anchorage pins in regions of a relatively higher proportion of bony tissue than in regions of a relatively lower proportion of bony tissue, wherein a surface density of the anchorage pins amounts to at least $3/cm^2$ and at most $30/cm^2$, wherein each of said anchorage pins is essentially freestanding in said longitudinal direction.

2. An implant in accordance with claim 1, wherein the implant comprises at least one of a proximal tibial implant and a distal femoral component of a knee joint prosthesis.

3. An implant in accordance with claim 1, wherein the implant comprises at least one of a proximal femoral component of a hip joint and an acetabular component of a hip joint, the proximal femoral component having a metal articulation surface.

4. An implant in accordance with claim 1, wherein the implant comprises a component of a shoulder joint prosthesis for anchorage to one of the scapula and the proximal humerus.

5. An implant in accordance with claim 1, wherein the implant comprises a component of an intervertebral implant.

6. An implant in accordance with claim 1, wherein said surface density is maintained over essentially the entire fastening side of the implant.

7. An implant in accordance with claim 6, wherein said anchorage pins are configured for implantation substantially only into spongious bone tissue.

8. An implant in accordance with claim 6, wherein the surface density is essentially constant for the plurality of anchorage pins and said anchoring pins are spaced no more than 3 mm apart.

9. An implant in accordance with claim 6, wherein the surface density is variable for the plurality of anchorage pins and said anchoring pins are spaced no more than 3 mm apart.

10. An implant in accordance with claim 6, wherein said anchorage pins include pins with length-diameter ratios of at least 8.

11. An implant in accordance with claim 1, wherein said anchorage pins are configured for implantation substantially only into spongious bone tissue.

12. An implant in accordance with claim 11, wherein cross-sections of said anchorage pins have circumscribed circles whose diameters amount to at most 1 mm at the base of the pins adjacent the fastening side of the implant.

13. An implant in accordance with claim 1, wherein said anchorage pins include pins with length-diameter ratios of at least 8.

14. An implant in accordance with claim 13, wherein said anchorage pins are configured for implantation substantially only into spongious bone tissue and said surface density is maintained over essentially the entire fastening side of the implant.

15. An implant for anchorage to a bone, wherein bony tissue comprises at least a portion of the total tissue of the bone, the implant comprising:
   a fastening side for arrangement adjacent to the bone; and
   a plurality of anchorage pins extending away from the fastening side for anchoring the implant in the bone, with at least one of a pin arrangement and a geometry of the plurality of anchorage pins being different in different regions of the fastening side of the implant and the volume of the anchorage pins per unit of area of the fastening side of the implant being different in different regions of the fastening side, with at least one of the pin arrangement and the geometry of the plurality of anchorage pins selected in accordance with the proportion of bony tissue to the total tissue of the bone opposite to which the fastening side is provided for implantation such that upon implantation a lower volume of tissue per unit of area of the fastening side of the implant will be displaced by the anchorage pins in regions of a relatively higher proportion of bony tissue than in regions of a relatively lower proportion of bony tissue, wherein said plurality of anchorage pins includes pins with length-diameter ratios of at least 8.

16. An implant in accordance with claim 15, wherein the volume of the anchorage pins per unit of area of the fastening side of the implant behaves substantially inversely proportional to the proportion of bony tissue to the total tissue of the bone opposite to which the fastening side is provided for implantation.

17. An implant in accordance with claim 15, wherein a surface density of the anchorage pins amounts to at least $3/cm^2$ and at most $30/cm^2$.

18. An implant in accordance with claim 17, wherein said anchorage pins point in essentially the same longitudinal direction and are all essentially freestanding in said longitudinal direction.

19. An implant in accordance with claim 18, wherein said surface density is maintained over essentially the entire fastening side of the implant and said anchorage pins are configured for implantation substantially only into spongious bone tissue.

20. An implant in accordance with claim 19, wherein said anchoring pins are spaced no more than 3 mm apart.

21. An implant for anchorage to a bone, wherein bony tissue comprises at least a portion of the total tissue of the bone, the implant comprising:
   a fastening side for arrangement adjacent to the bone; and
   a plurality of anchorage pins extending away from the fastening side for anchoring the implant in the bone, with at least one of a pin arrangement and a geometry of the plurality of anchorage pins being different in different regions of the fastening side of the implant and the volume of the anchorage pins per unit of area of the fastening side of the implant being different in different regions of the fastening side, with at least one of the pin arrangement and the geometry of the plurality of anchorage pins selected in accordance with the proportion of bony tissue to the total tissue of the bone opposite to which the fastening side is provided for implantation such that upon implantation a lower volume of tissue per unit of area of the fastening side of the implant will be displaced by the anchorage pins in regions of a relatively higher proportion of bony tissue than in regions of a relatively lower proportion of bony tissue, wherein said plurality of anchorage pins includes a non-peripheral group of anchorage pins adapted for implantation in said regions of a relatively lower proportion of bony tissue, with all of the anchorage pin in said group having cross-sections with circumscribed circles whose diameters amount to at most 1 mm at the base of the pins adjacent the fastening side of the implant.

22. An implant in accordance with claim 21, wherein a surface density of the anchorage pins of at least $3/cm^2$ and at most $30/cm^2$ is exhibited over essentially the entire fastening side of the implant and includes anchorage pins with length-diameter ratios of at least 8.

23. An implant for anchorage to a bone, wherein bony tissue comprises at least a portion of the total tissue of the bone, the implant comprising:
   a fastening side for arrangement adjacent to the bone; and
   a plurality of anchorage pins arranged on the fastening side and together extending away from the fastening side in essentially the same longitudinal direction for anchoring the implant in the bone, wherein each of said anchorage pins is essentially freestanding in said longitudinal direction, with at least one of a pin arrangement and a geometry of the plurality of anchorage pins being different in different regions of the fastening side of the implant and the volume of the anchorage pins per unit of area of the fastening side of the implant being different in different regions of the fastening side, with at least one of the pin arrangement and the geometry of the plurality of anchorage pins selected in accordance with the proportion of bony tissue to the total tissue of the bone opposite to which the fastening side is provided for implantation such that upon implantation a lower volume of tissue per unit of area of the fastening side of the implant will be displaced by the anchorage pins in regions of a relatively higher proportion of bony tissue than in regions of a relatively lower proportion of bony tissue, wherein said plurality of anchorage pins includes anchorage pins with length-diameter ratios of at least 8.

24. An implant in accordance with claim 23, wherein a surface density of the anchorage pins of at least $3/cm^2$ and at most $30/cm^2$ is exhibited over essentially the entire fastening side of the implant.

* * * * *

UNITED STATES PATENT AND TRADEMARK OFFICE
CERTIFICATE OF CORRECTION

PATENT NO. : 8,308,807 B2
APPLICATION NO. : 12/162729
DATED : November 13, 2012
INVENTOR(S) : Seebeck et al.

It is certified that error appears in the above-identified patent and that said Letters Patent is hereby corrected as shown below:

Title page, in column 2, under "Other Publications", line 1, delete "J.S. and P.C." and insert --J. S. and P. S.--, therefor On Title page 2, in column 1, under "U.S. Patent Documents", line 60, delete "7,001,431" and insert --7,001,131--, therefor Signed and Sealed this
Thirtieth Day of April, 2013

Teresa Stanek Rea
*Acting Director of the United States Patent and Trademark Office*